United States Patent [19]

Lang et al.

[11] Patent Number: 4,879,284
[45] Date of Patent: Nov. 7, 1989

[54] NAPHTHALENE DERIVATIVES HAVING RETINOID TYPE ACTION, THE PROCESS FOR PREPARATION THEREOF AND MEDICINAL AND COSMETIC COMPOSITIONS CONTAINING THEM

[75] Inventors: Gérard Lang, Saint-Gratien; Jean Maignan, Tremblay les Gonesse; Serge Restle, Aulnay Sous Bois; Gérard Malle, Villiers S/Morin, all of France

[73] Assignee: L'Oreal, Paris, France

[21] Appl. No.: 2,708

[22] PCT Filed: Apr. 14, 1986

[86] PCT No.: PCT/FR86/00123
   § 371 Date: Dec. 5, 1986
   § 102(e) Date: Dec. 5, 1986

[87] PCT Pub. No.: WO86/06064
   PCT Pub. Date: Oct. 23, 1986

[30] Foreign Application Priority Data

Apr. 15, 1985 [FR] France ................................ 85 05606

[51] Int. Cl.$^4$ .................... C07C 57/42; C07C 103/58; A61K 7/00; A61K 31/19
[52] U.S. Cl. ........................................ 514/62; 549/398; 549/404; 549/408; 546/187; 546/189; 546/196; 546/205; 546/206
[58] Field of Search .................. 514/62; 549/398, 404, 549/408; 546/187, 189, 196, 205, 206

[56] References Cited

U.S. PATENT DOCUMENTS 3,984,444 10/1976 Bollag et al. ................... 544/176
4,193,931  3/1980 Loeliger ........................ 568/633

OTHER PUBLICATIONS

Journal of the Chemical Society-Chemical Communications, No. 1, 1982, M. Akhtar et al.: "Interaction of a Conformationally Rigid Analogue of Retinal with Bacterio-Opsin", pp. 44–46, p. 44, alinéa 1; Formule 2.

FR, A, 2239996 (F. Hoffmann–La Roche) 7 Mars 1975, voir revendications 1,6,22–26.
Helvetica Chimica Acta, vol. 63, Fasc. 6, No. 168, (1980), P. Loeliger et al.: "Synthese Bicyclischer Retinoide aus Retinsäule", pp. 1604–1608, p. 1604, "Summary"; p. 1605, Formule 2.
Biochemistry, vol. 23, No. 5, 28 Février 1984, American Chemical Society, (U.S) Tatsuo Iwasa et al.: "Properties of an Analogue Pigment of Bacteriorhodopsin Synthesized with Naphthylretinal", pp. 838–843, voir, p. 838.

Primary Examiner—Ronald W. Griffin
Attorney, Agent, or Firm—Cushman, Darby & Cushman

[57] ABSTRACT

The invention relates to a compound of formula:

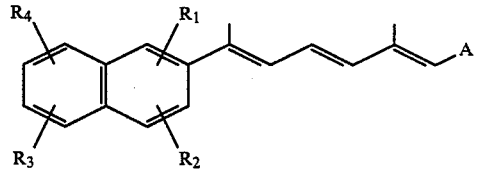

in which formula:
$R_1$ to $R_4$ denote, independently, H, OH, $C_1$–$C_6$ alkyl or $C_1$–$C_6$ alkoxy; and A denotes —$COR_5$, $R_5$ being H when at least one of the substituents $R_1$ to $R_4$ is other than H; $C_1$–$C_6$ alkyl; amino; ($C_1$–$C_6$)alkylamino; di($C_1$–$C_6$) alkylamino; arylamino; benzylamino; amino drived from a cyclic or heterocyclic amine; (—$COR_5$ being able, when it is an amide group, to be the amide group of an amino acid or of a glucosamine); or alternatively $R_5$ denotes —$OR_6$, $R_6$ being H or ($C_1$–$C_6$)alkyl; $C_1$–$C_6$ mono- or polyhydroxyalkyl, or aryl or benzyl, both optionally substituted; —$OR_6$ also being able to be derived from a sugar; and the salts and isomers of this compound. The invention also relates to a process for preparing this compound and medicinal and cosmetic compositions containing them.

18 Claims, No Drawings

NAPHTHALENE DERIVATIVES HAVING RETINOID TYPE ACTION, THE PROCESS FOR PREPARATION THEREOF AND MEDICINAL AND COSMETIC COMPOSITIONS CONTAINING THEM

The invention relates to new chemical compounds consisting of 2-substituted naphthalene derivatives and also to a preparation process by means of which these new compounds may be obtained. The invention also relates to the use of these new compounds, either in cosmetics or as pharmaceutical preparations in the treatment of dermatological conditions linked to a disorder of keratinization (differentiation/proliferation), in the treatment of dermatological or other conditions having an inflammatory and/or immuno-allergic component and in the treatment of atopy, whether cutaneous or respiratory, and also as pharmaceutical preparations for the ophthalmological field, in particular in the treatment of corneopathies.

The therapeutic action of vitamin A in its acid, aldhyde or alcohol form is well known in dermatology [in this connection, see the publication EXPERIENTIA, volume 34, pages 1105-1119 (1978)]; this action in the treatment of cutaneous proliferations, acne, psoriasis and similar conditions will be designated hereinafter by the generic term "retinoid type action". It was found that products having a structure analogous to vitamin A also showed a retinoid type action, but that the side effect of toxic hypervitaminosis could, for certain compounds, be boosted by a smaller factor than the boosting factor of the retinoid type effect sought (in this connection, see EUR. J. MED. CHEM.-CHIMICA THERAPEUTICA, Jan.-Feb. 1980, 15, No. 1, pages 9-15); in this latter publication, P. LOELIGER et al. described a derivative of formula (I):

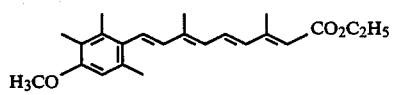

(I)

The unsaturated side chain of this compound of formula (I) is identical to that of natural retinoic acid of formula (II):

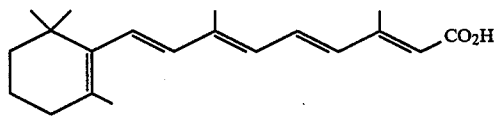

(II)

From German patent application Ser. No. 2,437,607, there is also known a family of compounds having retinoid type action corresponding to the general formula (III):

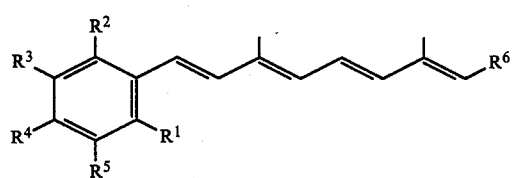

(III)

in which formula the substituents $R^3$ and $R^4$, inter alia, together form a benzene ring fused to the first ring, the compound of formula (III) then corresponding to a naphthalene derivative substituted at the 2-position with a 3,7-dimethyltetraene chain, which is the same as that in the abovementioned compounds (I) and (II).

From German Patent No. 3,121,091, a compound having anti-seborrhoeic action is also known, corresponding to the general formula (IV):

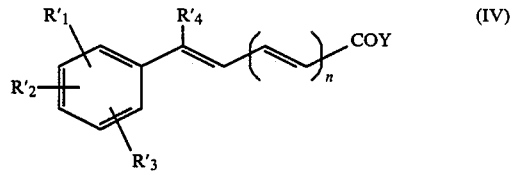

(IV)

in which formula n equals 0 or 1, which means that the side chain contains at most two double bonds, and in which $R'_1$ and $R'_2$ can form together a benzene ring fused to the first ring, so that the resulting compound is a naphthalene derivative substituted in the 2-position.

From U.S. Pat. No. 3,755,604, a method is known for decreasing sebum production by means of a 2-trans-4-trans-pentanedienoic acid of formula:

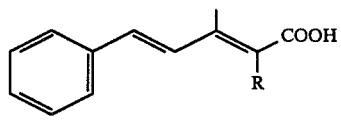

where R can represent hydrogen.

Finally, M. AKHTAR et al., in the publication J. CHEM. SOC., CHEM. COMMUN., 1982, page 44, have described the aldehyde of formula (V):

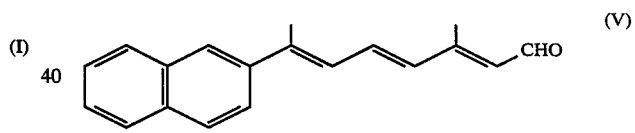

(V)

This publication gives no indication of the fact that the aldehyde of formula (V) might show any medicinal or cosmetic action.

It has been found, according to the invention, that the aldehyde of formula (V) shows a retinoic action and that it was possible to synthesise compounds of formula (V) modified by the presence of substituents on the naphthalene ring, and/or by the replacement of the aldehyde group by other groups, these compounds still enjoying the retinoid action.

The subject of the invention is hence the new industrial product represented by a new chemical compound corresponding to the general formula (VI):

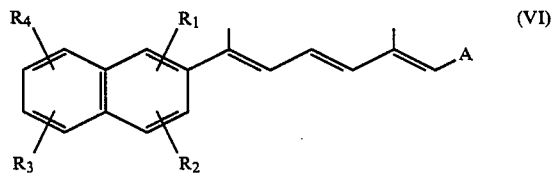

(VI)

in which formula:

$R_1$, $R_2$, $R_3$ and $R_4$, which can be distributed on either of the rings or on both at once, denote, independently, a hydrogen atom, a linear or branched $C_1$-$C_6$ alkyl radical, a hydroxyl group or a $C_1$-$C_6$ alkoxy radical; and A denotes a group —$COR_5$ in which $R_5$ is:

(a) a hydrogen atom when at least one of the substituents $R_1$ to $R_4$ is other than hydrogen; a $C_1$-$C_6$ alkyl radical; an amino radical; an alkylamino radical or a dialkylamino radical, the alkyl residue in these monoalkylamino or dialkylamino radicals containing from 1 to 6 carbon atoms and being able to be substituted with one or more hydroxyl groups and/or being able to be interrupted by one or more hetero atom(s) such as oxygen, nitrogen or sulphur; an arylamino radical; a benzylamino radical; or an amino radical derived from a cyclic or heterocyclic amine; the group —$COR_5$ being able, in addition, when it is an amide group, to be the amide group of an amino acid or of a glucosamine;

(b) a group —$OR_6$ in which $R_6$ is a hydrogen atom, a $C_1$-$C_6$ alkyl radical, a $C_1$-$C_6$ mono- or polyhydroxyalkyl radical, an optionally substituted aryl radical or an optionally substituted benzyl radical, the group —$OR_6$ also being able to be derived from a sugar; and the salts and isomers of this chemical compound.

Among $C_1$-$C_6$ alkyl radicals which are especially usable within the meanings of the radicals $R_1$ to $R_4$ mentioned above, methyl, ethyl, isopropyl, butyl, isobutyl and hexyl radicals may be mentioned.

When A denotes a group —$COOR_6$, the group —$OR_6$ being derived from a sugar, the latter is chosen, in particular, from the group composed of glucose, mannitol and erythritol.

The compounds of formula (VI) or their isomers, when they take the form of their salts, are advantageously zinc salts, alkali metal or alkaline earth metal salts or salts of an organic amine, the compounds of formula (VI) then containing at least one free acid group.

Among the compounds of formula (VI), those are preferred which correspond to the following formula (VI'):

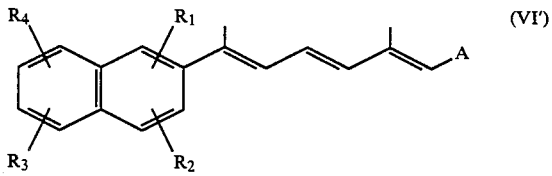

in which formula:

$R_1$, $R_2$, $R_3$ and $R_4$, which can be distributed on either of the two rings or on both at once, denote H, a $C_1$-$C_6$ alkyl or an alkoxy radical, at least two being other than H; and A denotes:

(a) —$COR_5$, $R_5$ being an amino or mono— or dialkylamino radical, or (b) —$COOR_6$, $R_6$ having the meanings stated above.

The subject of the invention is also a process for preparing the new compounds of formula (VI). According to this process, the synthesis is carried out by the Witting reaction; the process hence consists, in the final stage, in reacting a substituted or unsubstituted 2-[1-(triphenylphosphonio)ethyl]naphthalene salt with an aldehyde RCHO in basic medium, according to the reaction:

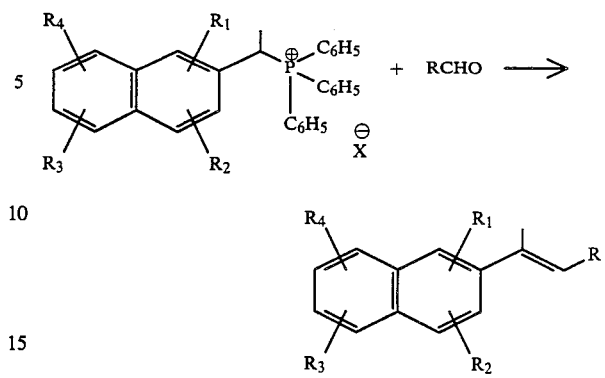

$R_1$, $R_2$, $R_3$ and $R_4$ having the meanings stated above, X denoting a halogen atom, and R denoting the substituent chain of formula (VII):

in which A has the meaning stated above.

2-[1-(Triphenylphosphonio)ethyl]naphthalene salts are known compounds which can advantageously be obtained in the following manner:

(a) in a first stage, the naphthalene ring-system is acylated using a Friedel-Crafts reaction;

(b) in a second stage, the acylnaphthalene obtained is reduced by means of sodium borohydride to obtain the corresponding alcohol;

(c) in a third stage, a phosphorus trihalide $PX_3$ is reacted with the said alcohol to obtain a 2-(1-haloethyl)-naphthalene;

(d) in a fourth stage, approximately one equivalent of triphenylphosphine is reacted to obtain the desired salt.

This entire preparation can be represented by the working scheme below:

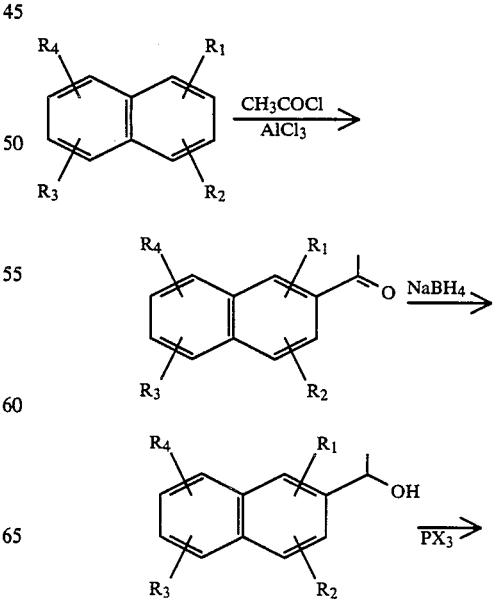

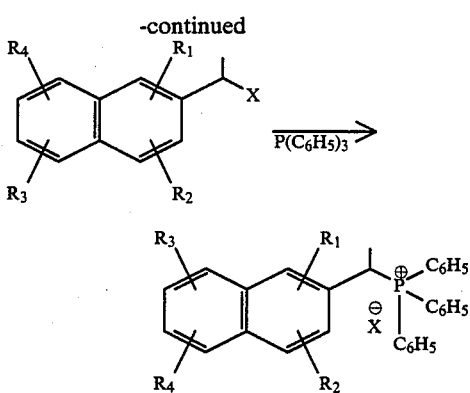

Among the aldehydes RCHO which can be used, there may be mentioned ethyl 5-formyl-3-methyl-2,4-pentadienoate, which is synthesized in two stages as described in the abovementioned publication EXPERIENTIA 1978, 34, pages 1105-1119 (also see CHEMICAL ABSTRACTS 57, 2056b and 58, 10066e); in this process, pyruvaldehyde dimethyl acetal and triethyl phosphonoacetate, which are both commercial products, are reacted in tetrahydrofuran in the presence of sodium hydride. An unsaturated ester is thereby obtained, with which vinyl ethyl ether is condensed in the presence of boron trifluoride etherate; the condensation product is then hydrolyzed with phosphoric acid and the aldehyde obtained is purified by recrystallization.

The compound of formula (VI) obtained by the preparation process according to the invention can undergo functional modifications of the substituent A. Among the functional modifications of this substituent A, the preparation, for example, of alcohols, acids and their salts, and amides, from the corresponding esters, will be mentioned. All these functional modifications can be carried out by procedures known per se.

The compounds of formula (VI) are obtained in the state of cis/trans mixtures which, if so desired, can be separated in a manner known per se into pure cis and trans compounds.

According to the invention, it has been found that the compounds of formula:

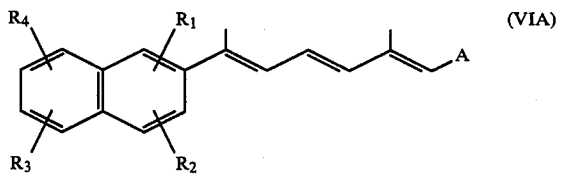

in which formula:

$R_1$, $R_2$, $R_3$ and $R_4$, which can be distributed on either of the rings or on both at once, denote, independently, a hydrogen atom, a linear or branched $C_1$-$C_6$ alkyl radical, a hydroxyl group or a $C_1$-$C_6$ alkoxy radical; and A denotes a group —$COR_5$ in which $R_5$ is:

(a) a hydrogen atom; a $C_1$-$C_6$ alkyl radical; an amino radical; an alkylamino radical in which the alkyl residue contains from 1 to 6 carbon atoms and can be substituted with one or more hydroxyl groups and/or interrupted by one or more hetero atoms such as oxygen, nitrogen or sulphur; a dialkylamino radical in which each alkyl residue contains from 1 to 6 carbon atoms and can be substituted with one or more hydroxyl groups and/or interrupted by one or more hetero atoms such as oxygen, nitrogen or sulphur; an arylamino radical; a benzylamino radical; or an amino radical derived from a cyclic or heterocyclic amine; the group —$COR_5$ being able, in addition, when it is an amide group, to be the amide group of an amino acid or of a glucosamine;

(b) a group —$OR_6$ in which $R_6$ is a hydrogen atom, a $C_1$-$C_6$ alkyl radical, a $C_1$-$C_6$ mono- or polyhydroxyalkyl radical, an optionally substituted aryl radical or an optionally substituted benzyl radical, the group —$OR_6$ also being able to be derived from a sugar; and the salts and isomers of these compounds have a retinoic action and are especially well suited to the treatment of the dermatological conditions linked to a disorder of keratinization (differentiation/proliferation), as well as dermatological or other conditions having an inflammatory and/or immuno-allergic component, in particular the treatment of acne vulgaris, comedonic or polymorphic acnes, senile acnes, acne solaris and acne medicamentosa or trade acnes, extensive and/or severe forms of psoriasis, and other disorders of keratinization, in particular ichthyoses and ichthyosiform states, Darier's disease, keratoderma palmaris et plantaris, leukoplakia and leukoplakiform states, lichen planus, and all benign or malignant, severe or extensive dermatological proliferations; they are also active for certain rheumatic conditions, in particular psoriatic rheumatism; they can also be used in the treatment of cutaneous atopy such as eczema or respiratory atopy; they can also be recommended in epidermolysis bullosa dystrophica and in the molecular pathology of collagen; they also find an indication in ultraviolet-induced carcinomas (solar carcinogenesis), in epidermodysplasia verruciformis and related forms; and finally, they find application in the ophthalmological field, in particular for the treatment of corneopathies.

The subject of the present invention is hence also a new medicinal composition, intended in particular for the treatment of the abovementioned conditions, characterized in that it contains, as active substance(s), at least one compound of formula (VIA) and/or at least one of its isomers and/or at least one of its salts, in a pharmaceutically acceptable carrier.

Good activity of the compounds of formula (VIA) is observed over a very wide dilution range; in particular, concentrations of active substance(s) ranging from 0.0005% to 2% by weight can be used. It is naturally possible to use higher concentrations when this is necessitated for a particular therapeutic application; however, the preferred concentrations of active principle are between 0.01% and 1% by weight.

When the compounds of formula (VIA) are used topically, they advantageously take the form of ointments, gels, creams, pomades, powders, tinctures, solutions, suspensions, emulsions, lotions, sprays, patches or impregnated pads. The compounds in question are mixed with non-toxic inert carriers, generally liquid pasty, which are suitable for topical treatment. Solutions containing approximately 0.01% to 0.3% by weight of active substance(s) and creams containing approximately 0.02% to 0.5% by weight of active substance(s) may advantageously be used.

The abovementioned pharmaceutically active substances can be used enterally. Orally, the said active substances are administered in the proportion of approximately 2 μg to 2 mg per day per kg of body weight; an excessive dosage can manifest itself in the form of a hypervitaminosis A which can be recognized by its symptoms and give rise to fears regarding liver toxicity, requiring biological monitoring of hepatic function. The requisite dosage can be administered in one or more doses. For oral administration, the appropriate forms are, for example, tablets, gelatin capsules, dragées, syrups, suspensions, emulsions, solutions, powders and granules; a preferred mode of administration consists in using gelatin capsules containing from 0.1 mg to approximately 1 mg of active substance.

The pharmaceutically active substances can also be administered parenterally in the form of solutions or suspensions for intravenous or intramuscular perfusion or injection. In this case, the said active substances are administered in the proportion of approximately 2 µg to 2 mg per day per kg of body weight; a preferred mode of administration consists in using solutions or suspensions containing from 0.01 mg to approximately 1 mg of active substance(s) per ml.

When the pharmaceutically active substances are used for application to the eye, they advantageously take the form of solutions or powders to be diluted for eye lotions.

The pharmaceutically acceptable carrier can comprise water, gelatin, lactose, starch, talc, vaseline, gum arabic, polyalkylene glycols or magnesium stearate. The tablets, powders, dragées, granules or gelatin capsules can contain binders, fillers or pulverulant carriers. The solutions, creams, suspensions, emulsions or syrups can contain diluents, solvents or thickeners.

The compounds of the formula (VIA), as well as the salts and isomers of these compounds, also find application in the cosmetic field, especially in body and hair hygiene and, in particular, in the treatment of skin which tends to be affected by acne, dry skin, seborrhoea and hair loss, to promote the regrowth of hair and for treatment against the deleterious effects of sunlight.

The subject of the present invention is hence also a new cosmetic composition, characterized in that it contains, as active substance(s), at least one compound of formula (VIA) and/or at least one of its isomers and/or at least one of its salts, in a cosmetically acceptable carrier; this composition can take the form of lotions, gels, creams, soaps, shampoos or the like.

The concentration of cosmetically active substance(s) is between 0.0005 and 2% by weight, and preferably between 0.01 and 1% by weight, relative to the total weight of the composition.

In the treatment of the abovementioned disorders, the compounds according to the invention, used in the compositions defined above, act by increasing the follicular epithelial production of the non-adherent cells thereby dislodging and causing the removal of the content of the acne comedon. These compounds reduce the size of the sebaceous glands and partially inhibit the secretion of sebum.

The compounds according to the invention can contain inert, or even pharmacodynamically or cosmetically active additives, and in particular moisturizing agents, such as thiamorpholinone and its derivatives or urea; anti-seborrhoeic or anti-acne agents, such as S-carboxymethylcysteine, S-benzylcysteamine and their derivatives, tioxolone and benzoyl peroxide; antibiotics, such as erythromycin and its esters, neomycin, tetracyclines and isothiazolinones; agents promoting regrowth of hair, such as minoxidil (2,4-diamino-6-piperidinopyrimidine 3-oxide) and its derivatives, anthralin and its derivatives, diazoxide, phenytoin and oxapropanium iodide; nicotinic acid and its esters; anti-inflammatory agents (steroid or non-steroid); carotenoids and, in particular, β-carotene; and anti-psoriatic agents, such as anthralin and its derivatives and eicosa-5,8,11,14-tetraynoic and -5,8,11-triynoic acids, their esters and their amides.

The compounds according to the invention can also contain flavouring agents, preservatives, stabilizers, moisture-regulating agents, pH-regulating agents, osmotic pressure-modifying agents, emulsifiers, UV-B and UV-A filters and antioxidants such as α-tocopherol, butylated hydroxyanisole or butylated hydroxytoluene.

To enable the subject of the invention to be more readily understood, several embodiments thereof will now be described.

Example A, which is described below, does not form part of the invention and corresponds to the preparation of 6,7-dimethyl-2-[1-(triphenylphosphonio)ethyl]-naphthalene bromide.

2-[1-(Triphenylphosphonio)ethyl]naphthalene bromide, 1,4-dimethyl-2-[1-(triphenylphosphonio)ethyl]-naphthalene bromide, 3,7-dimethyl-2-[1-(triphenylphosphonio)-ethyl]naphthalene bromide and 5,8-dimethyl-6-methoxy-2-[1-(triphenylphosphonio)ethyl]naphthalene bromide are prepared in the same manner starting, instead of with 2-acetyl-6,7-dimethylnaphthalene, with 2-acetylnaphthalene, 2-acetyl-1,4-dimethylnaphthalene, 2-acetyl-3,7-dimethylnaphthalene and 2-acetyl-5,8-dimethyl-6-methoxynaphthalene, respectively, this latter being prepared according to a method described by M. FETIZON et al., Bull. Soc. Chim. Fr., 30 28, 1975, by treating 1,4-dimethyl-1,4-epoxy-1,4-dihydronaphthalene in methanol in the presence of concentrated hydrochloric acid.

This 1,4-dimethyl-1,4-epoxy-1,4-dihydronaphthalene is itself prepared by a cyclo addition reaction of benzene to 2,5-dimethylfuran, according to the method of M.S. NEWMANN et al., J. O. C., 40(2), 262–4 (1975).

The preparation examples 1 to 8 lead to compounds according to the invention all having the trans structure.

EXAMPLE A

Preparation of 6,7-dimethyl-2-[1-(triphenylphosphonio)ethyl]naphthalene bromide First stage: preparation of 2-acetyl-6,7-dimethylnaphthalene.

100 g of 2,3-dimethylnaphthalene are added in small portions in the course of approximately one hour to a mixture of 94 g of aluminium chloride (10.70 mol) and 50 cm$^3$ of acetyl chloride (0.70 mol), stirred under an inert atmosphere in one litre of dichloromethane. Stirring is maintained for 5 hours after the addition is complete. The reaction mixture is then poured with stirring into water.

The organic phase is decanted, washed until the washing liquors are neutral and dried over magnesium sulphate.

On evaporation of the methylene chloride in a rotary evaporator, 65 g of 2-acetyl-6,7-dimethylnaphthalene are obtained after drying and recrystallization in hexane.

Second stage: preparation of 6,7-dimethyl-2-(1-hydroxyethyl)naphthalene.

Two equivalents of sodium borohydride are added in small portions to a solution of 50 g of 2-acetyl-6,7-dimethylnaphthalene (0.26 mol) in 500 cm³ of methanol, stirred at room temperature and under an inert atmosphere. The temperature is maintained below 50° C. by means of an icebath. One hour after the addition is complete, all the starting material is converted.

400 cm³ of water are then added to the mixture. The methanol is evaporated off under reduced pressure. The aqueous phase is then neutralized by adding hydrochloric acid, and then extracted with ether. The organic phase is washed, dried over magnesium sulphate and concentrated. 45 g of a viscous liquid are obtained, the nuclear magnetic resonance spectrum of which corresponds to the expected structure.

Third stage: preparation of
2-(1-bromoethyl)-6,7-dimethylnaphthalene 36 cm³ of phosphorus tribromide are added dropwise at room temperature, under an inert atmosphere, to a solution, in 500 cm³ of dichloromethane, of 50 g of the alcohol prepared in the second stage.

After three hours' stirring at room temperature, the reaction mixture is left overnight. The excess reagent is destroyed by adding 200 cm³ of water. The organic phase is decanted, washed several times with water, dried over sodium sulphate and then evaporated under reduced pressure. After prolonged drying, 60 g of 2-(1-bromoethyl)-6,7-dimethylnaphthalene are obtained.

Fourth stage: preparation of
6,7-dimethyl-2-[1-(triphenylphosphonio)ethyl]naphthalene bromide 1.1 equivalent of triphenylphosphine is added at room temperature to a solution of 50 g of the compound prepared in the third stage in 300 cm³ of toluene. The mixture is then brought with stirring to the boiling point of toluene for 48 hours. The triphenylphosphonium bromide precipitates as it is formed. At the end of the reaction, it is filtered with suction and then dried.

90 g of 6,7-dimethyl-2-[1-(triphenylphosphonio)ethyl]naphthalene bromide are thereby obtained.

EXAMPLE 1

Preparation of ethyl
all-trans-7-(2-naphthyl)-3-methyl-2,4,6-octatrienoate

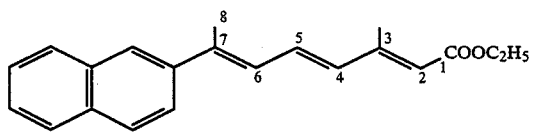

30 g (0.06 mol) of 2-[1-(triphenylphosphonio)ethyl]naphthalene bromide and 30 g of potassium carbonate are suspended in 750 cm³ of isopropanol. The reaction mixture is heated to 60° C. and 10 g (0.06 mol) of ethyl 5-formyl-3-methyl-2,4-pentadienoate are added under an inert atmosphere and shielded from the light. After the addition, the mixture is heated for 5 hours at the refluxing temperature of isopropanol, until the aldehyde has disappeared. The reaction medium is filtered hot. The filtrate is concentrated to half volume under reduced pressure and cooled in an icebath. The expected product crystallizes and 9.5 g of ester are recovered, the ¹H nuclear magnetic resonance spectrum of which is in agreement with the expected structure. The melting point of the said ester is 99°–101° C.

EXAMPLE 2

Preparation of
all-trans-7-(2-naphthyl)-3-methyl-2,4,6-octatrianoic acid

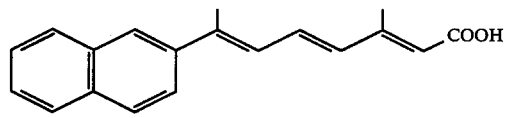

9.5 g of the ester of Example 1 is suspended in a mixture of 100 cm³ of ethanol and 100 cm³ of 6N aqueous potassium hydroxide. The reaction medium is brought to 50° C. shielded from the light, until the starting ester has completely disappeared. The ethanol is evaporated off under reduced pressure, and the aqueous phase is diluted to half concentration and acidified with 5N hydrochloric acid. The expected product crystallizes. 6.6 g of pure all-trans acid is recovered after recrystallization in an ethyl acetate/acetic acid mixture. The melting point of the product is 208°–210° C.

ELEMENTARY ANALYSIS

|  | C | H | O |
|---|---|---|---|
| Calculated for $C_{19}H_{18}O_2$ | 81.98 | 6.52 | 11.50 |
| Found | 81.80 | 6.52 | 11.42 |

EXAMPLE 3

Preparation of ethyl
all-trans-7-(1,4-dimethyl-2-naphthyl)-3-methyl-2,4,6-octatrianoate

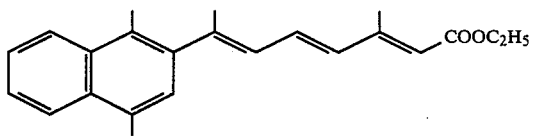

39 g (0.0743 mol) of 1,4-dimethyl-2-[1-(triphenylphosphonio)ethyl]naphthalene bromide are suspended in 250 cm³ of anhydrous tetrahydrofuran. The mixture is cooled to 0° C. and 40 cm³ of 2.5 M n-butyllithium are added under an inert atmosphere until the starting salt has been completely solubilized. The mixture is stirred for 1 hour, and then 10 cm³ of dichloromethane are added dropwise, shielded from the light, to destroy the excess n-butyllithium, followed by 15 g of ethyl 5-formyl-3-methyl-2,4-pentadianoate dissolved in the minimum of dichloromethane. The reaction mixture is allowed to return to room temperature overnight, and is the acidified with 15 cm³ of acetic acid in 75 cm³ of tetrahydrofuran. The solvent is evaporated off under reduced pressure and the residue taken up with 500 cm³ of water. After extraction with ethyl acetate and purification by chromatography on silica gel, 9.5 g of the expected ester are recovered, the ¹H nuclear magnetic resonance spectrum of which is in agreement with the expected structure. The melting point of the said ester is 72° C.

EXAMPLE 4

Preparation of all-trans-7-(1,4-dimethyl-2-naphthyl)-3-methyl-2,4,6-octatrianoic acid

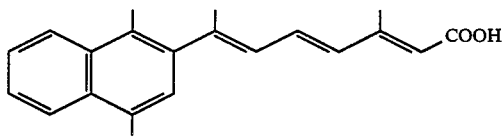

9 g of the ester obtained in Example 3 are suspended in a mixture of 100 cm³ of ethanol and 100 cm³ of 6N aqueous potassium hydroxide. The reaction medium is brought to 50° C., shielded from the light, until the starting ester has completely disappeared. The ethanol is evaporated off under reduced pressure, and the residue poured into 250 cm³ of water and acidified with 5N hydrochloric acid. The expected product crystallizes. 5 g of pure all-trans acid are recovered after recrystallization in methanol. The melting point of the product is 218°–220° C.

ELEMENTARY ANALYSIS

|  | C | H | O |
|---|---|---|---|
| Calculated for $C_{21}H_{22}O_2$ | 82.32 | 7.24 | 10.44 |
| Found | 82.28 | 7.26 | 10.55 |

EXAMPLE 5

Preparation of ethyl all-trans-7-(6,7-dimethyl-2-naphthyl)-3-methyl-2,4,6-octatrianoate

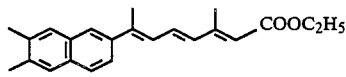

15 cm³ of n-butyllithium (1.6 M) are added dropwise under an inert atmosphere and at 0° C. to a suspension of 10.5 g (0.02 mol) of 6,7-dimethyl-2-[1-(triphenylphosphonio)ethyl]naphthalene bromide, prepared in Example A, in 60 cm³ of anhydrous tetrahydrofuran, until the starting salt has been completely solubilized. The mixture is stirred for 30 minutes, and this is followed by the addition of 1 cm³ of dichloromethane to destroy the excess n-butyllithium and 3.3 g of ethyl 5-formyl-3-methyl-2,4-pentadianoate dissolved in the minimum of dichloromethane. The reaction medium is allowed to return to room temperature and, after 2 hours' stirring, is acidified with acetic acid. The mixture is poured into 300 cm³ of water, extracted with ethyl acetate and purified by chromatography on silica gel. 3 g of the expected product are recovered after recrystallization in methanol. The ¹H nuclear magnetic resonance spectrum is in agreement with the expected structure. The product melts at 104° C.

EXAMPLE 6

Preparation of all-trans-7-(6,7-dimethyl-2-naphthyl)-3-methyl-2,4,6-octatrianoic acid

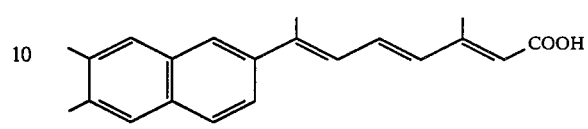

2.5 g of the ester of Example 5, suspended in 75 cm³ of an ethanol/6N aqueous potassium hydroxide (50:50) mixture, are heated to 50° C. until the starting ester has completely disappeared. The ethanol is evaporated off under reduced pressure, the residue is poured into 100 cm³ of water and a first extraction is performed with ether. The aqueous phase is acidified with 5N hydrochloric acid and the expected product is extracted with ether. 1.1 g of pure all-trans acid is recovered after recrystallization in methanol. The melting point of this acid is 202°–203° C.

ELEMENTARY ANALYSIS

|  | C | H | O |
|---|---|---|---|
| Calculated for $C_{21}H_{22}O_2$ | 82.32 | 7.24 | 10.44 |
| Found | 82.36 | 7.27 | 10.49 |

EXAMPLE 7

Preparation of ethyl all-trans-7-(3,7-dimethyl-2-naphthyl)-3-methyl-2,4,6-octatrianoate

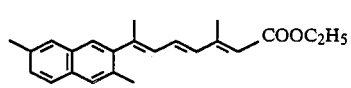

7 cm³ of 1.6 M n-butyllithium are added dropwise under an inert atmosphere and at 0° C. to a suspension of 5.2 g (0.01 mol) of 3,7-dimethyl-2-[1-(triphephenylphosphonio)ethyl]naphthalene bromide in 30 cm³ of anhydrous tetrahydrofuran, until the starting salt has been completely solubilized. The mixture is stirred for 30 minutes, and 1 cm³ of dichloromethane is then added, shielded from the light, followed by 1.7 g of ethyl 5-formyl-3-methyl-2,4-pentadianoate dissolved in the minimum of dichloromethane. The mixture is allowed to return to room temperature and, after 3 hours' stirring, is acidified with acetic acid. The mixture is poured into 150 cm³ of water and extracted with ethyl acetate, and the product is purified by chromatography on silica gel. 1.2 g of pure product is recovered after recrystallization in methanol. The ¹H nuclear magnetic resonance spectrum is in agreement with the expected structure. The product melts at 131°–133° C.

EXAMPLE 8

Preparation of all-trans-7-(3,7-dimethyl-2-naphthyl)-3-methyl-2,4,6-octatrianoic acid

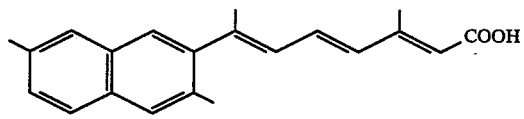

1.1 g of the ester of Example 7, suspended in 35 cm³ of an ethanol/6N aqueous potassium hydroxide (50:50) mixture, is brought to 50° C. and heated until the starting ester has completely disappeared. The ethanol is evaporated off under reduced pressure and the residue poured into 100 cm³ of water and extracted a first time with ether. The aqueous phase is acidified with 5N hydrochloric acid and the expected product crystallizes. 540 mg of pure all-trans acid are recovered after recrystallization in methanol. The melting point of the product is 226° C.

ELEMENTARY ANALYSIS

|  | C | H | O |
|---|---|---|---|
| Calculated for $C_{21}H_{22}O_2$ | 82.32 | 7.24 | 10.44 |
| Found | 82.40 | 7.21 | 10.30 |

EXAMPLE 9

Preparation of ethyl all-trans-7-(5,8-dimethyl-6-methoxy-2-naphthyl)-3-methyl-2,4,6-octatrianoate

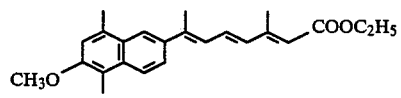
(a)

and ethyl all-trans-7-(5,8-dimethyl-6-hydroxy-2-naphthyl)-3-methyl-2,4,6-octatrianoate

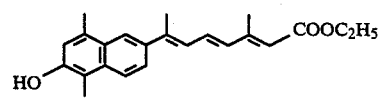
(b)

5 cm³ of butyllithium (2.5 M in hexane) are added slowly to a suspension of 5,8-dimethyl-6-methoxy-2-[1-(triphenylphosphonio)ethyl]naphthalene bromide in 70 cm³ of tetrahydrofuran stirred under an atmosphere of argon at −30° C. After 30 minutes, the excess butyllithium is destroyed by adding 2 cm³ of dichloromethane. A solution of 1.9 g (11.3 mmol) of ethyl 5-formyl-3-methyl-2,4-pentadianoate in 20 cm³ THF is then added at a temperature of −10° C. in the course of approximately 30 minutes. After 3 hours' stirring at 0° C., the reaction is complete. 100 cm³ of N hydrochloric acid are then added to the mixture at −30° C. The organic phase is decanted, washed with water and dried over sodium sulphate.

After evaporation and drying, the expected product is purified by chromatography on silica gel. Eluting with a hexane/ether (80:20) mixture, the ethyl alltrans-7-(5,8-dimethyl-6-methoxy-2-naphthyl)-3-methyl-2,4,6-octatrianoate is carried through. After evaporation of the eluant, 1.4 g of product is obtained, which product is recrystallized in 40 cm³ of methanol. 1 g of yellow crystals is thereby isolated, the melting point of which is 101° C.

Using a more polar eluant toluene/dichloromethane/ethyl acetate (5:3:2), the ethyl all-trans-7-(5,8-dimethyl-6-hydroxy-2-naphthyl)-3-methyl-2,4,6-octatrianoate is carried through. After evaporation of the solvent, 0.5 g of product is obtained, which product is recrystallized in a toluene/hexane mixture. 0.35 g of yellow crystals is thereby isolated, the melting point of which is 139° C.

EXAMPLE 10

Preparation of all-trans-7-(5,8-dimethyl-6-methoxy-2-naphthyl)-3-methyl-2,4,6-octatrianoic acid

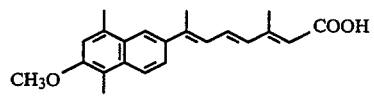

A suspension of 0.7 g (2 mmol) of ethyl all-trans-7-(5,8-dimethyl-6-methoxy-2-naphthyl)-3-methylocatatrianoate is stirred for 2 hours at 70° C. in a mixture of 10 cm³ of ethanol and 10 cm³ of 6N aqueous potassium hydroxide. 50 cm³ of water are added to the mixture and the alcohol is evaporated off under reduced pressure. The aqueous phase is diluted by adding 60 cm³ of water, and then acidified at 5° C. by adding 10 cm³ of concentrated hydrochloric acid. The precipitate is filtered with suction, washed with water and then dried, and recrystallized in a mixture of 30 cm³ of acetonitrile and 90 cm³ of acetone. 0.5 g of all-trans-7-(5,8-dimethyl-6-methoxy-2-naphthyl)-3-methyl-2,4,6-octatrianoic acid is thereby isolated in the form of yellow crystals, the melting point of which is 256° C.

ELEMENTARY ANALYSIS

|  | C | H | O |
|---|---|---|---|
| Calculated for $C_{22}H_{24}O_3$ | 78.54 | 7.19 | 14.27 |
| Found | 78.20 | 7.44 | 14.35 |

EXAMPLE 11

Preparation of ethyl all-trans-7-(5,8-dimethyl-6-methoxy-2-naphthyl)-3-methyl-2,4,6-octatrianoate and its (2E, 4E, 6Z)-isomer A suspension is prepared of 17.6 g (0.032 mol) of [1-(5,8-dimethyl-6-methoxy-2-naphthyl)ethyl]triphenylphosphonium bromide and 8.8 g (0.064 mol) of potassium carbonate in 250 cm³ of isopropanol. This suspension is brought to 70° C. and 5.4 g (0.032 mol) of ethyl 5-formyl-3-methyl-2,4-pentadianoate are added under an inert atmosphere and shielded from the light, and the mixture is heated for approximately 4 hours to the refluxing temperature of isopropanol until the aldehyde has disappeared. The mixture is then filtered hot on silica: the filtrate is concentrated under reduced pressure. The residue is solubilized in the minimum of hot methanol. 5.4 g of ester are obtained on crystallization, which ester is in fact a mixture of the two isomers.

Carrying out a recrystallization in approximately 160 cm³ of methanol, a first 4.1-g fraction of ethyl all-trans-7-(5,8-dimethyl-6-methoxy-2-naphthyl)-3-methyl-2,4,6-octatrianoate is obtained, the physical characteristics of which are identical to those of the product obtained in Example 9. By concentrating the filtrates, a second 1.2-g fraction of an ester is obtained, the melting point of which is 118°–119° C. and the ¹H nuclear magnetic resonance spectrum of which corresponds to the structure ethyl (2E, 4E, 6Z)-7-(5,8-dimethyl-6-methoxy-2-naphthyl)-3-methyl-2,4,6-octatrianoate.

EXAMPLE 12

Preparation of (2E, 4E, 6Z)-7-(5,8-dimethyl-6-methoxy-2-naphthyl)-3-methyl-2,4,6-octatrianoic acid.

A suspension is made of 1 g of ethyl (2E, 4E, 6Z)-7-(5,8-dimethyl-6-methoxy-2-naphthyl)-3-methyl-2,4,6-octatrianoate, obtained in Example 11, in a mixture of 50 cm³ of ethanol and 50 cm³ of 6N aqueous potassium hydroxide; this suspension is then heated to 50° C., shielded from the light, until the starting ester has completely disappeared. The ethanol is then evaporated off under reduced pressure; the aqueous phase is diluted to half concentration and acidified with 5N hydrochloric acid, and the expected product crystallizes. 600 mg of the expected pure acid are recovered after recrystallization in methyl ethyl ketone. The melting point of this acid is 248°–249° C.

ELEMENTARY ANALYSIS

|  | C | H | O |
|---|---|---|---|
| Calculated for $C_{22}H_{24}O_3$ | 78.54 | 7.19 | 14.27 |
| Found | 78.35 | 7.22 | 13.99 |

EXAMPLE 13

Preparation of all-trans-N-ethyl-7-(5,8-dimethyl-6-methoxy-2-naphthyl)-3-methyloctatrienamide 1.95 g of 1,1-paracarbonyldiimidazole is added to a solution of 2 g of all-trans-7-(5,8-dimethyl-6-methoxy-2-naphthyl)-3-methyl-2,4,6-octatrianoic acid, obtained in Example 10, in 150 cm³ of anhydrous dimethylformamide, and this reaction medium is heated to 50° C. for three hours. After the mixture is cooled to 0° C., a large excess (approximately 5 cm³) of anhydrous ethylamine is added and the mixture is stirred for 12 hours at room temperature. The reaction medium is then poured into 500 cm³ of water and extracted with ethyl acetate. The organic phase is washed with 100 cm³ of water, dried over magnesium sulphate and concentrated under reduced pressure. 750 mg of the expected product is recovered by recrystallization in toluene. This product melts at 194°–195° C. and the ¹H nuclear magnetic resonance spectrum corresponds to the expected structure.

ELEMENTARY ANALYSIS

|  | C | H | N | O |
|---|---|---|---|---|
| Calculated for $C_{24}H_{29}NO_2$ | 79.30 | 8.04 | 3.85 | 8.80 |
| Found | 79.23 | 8.06 | 3.89 | 9.04 |

EXAMPLE 14

The following composition, which contains 0.05% of active product and is intended to be packaged in a capsule, is prepared:

| Compound of Example 8 | 0.25 mg |
|---|---|
| Liquid paraffin qs | 0.5 ml |

The capsules used are soft capsules, the envelope of which has the following formulation:

| Gelatin, pharmaceutical grade | 53.0 g |
|---|---|
| Glycerin | 17.0 g |
| Sorbitol, 70% strength | 17.0 g |
| Gum arabic | 13.0 g |
| Sweetener qs | |
| Opacifier (TiO₂) qs | |
| Preservative qs | |

In this suspension, the compound of Example 8 can be replaced by that of Example 2 or that of Example 10.

The constituents are mixed hot. The mixture obtained is concentrated hot until the desired consistency is achieved. The filling of each capsule with the above-mentioned suspension is carried out by injecting the active liquid between two walls of sheathing, followed by simultaneous welding and cutting.

2 capsules per day are administered to an adult individual for the treatment of psoriatic rheumatism, and a significant improvement is noted after approximately 30 days.

EXAMPLE 15

The following formulation, consisting of a powder containing 0.1% of active product and packaged in a gelatin capsule, is prepared:

| Compound of Example 6 or 9a | 0.3 mg |
|---|---|
| Magnesium stearate | 3.0 mg |

Silica sold under the trade name

| "AEROSOL 200" by "DEGUSSA" | 30.0 mg |
|---|---|
| Lactose qs | 0.3 ml |

The gelatin capsules used have a No. 3 gauge opaque standard shell.

1 to 3 capsules per day are administered to an adult individual for the treatment of psoriasis, and a significant improvement is noted after approximately 30 days.

EXAMPLE 16

The following formulation, consisting of an aqueous solution containing 0.3% of active product and intended to be packaged in a 10-ml ampoule of solution to be taken by mouth, is prepared.

| Compound of Example 4 or 9a | 0.03 g |
|---|---|
| Sorbitol monooleate polyoxyethyleneated with 20 moles of ethylene oxide, sold under the tradename "POLYSORBATE 80" | 0.10 g |
| Sodium saccharinate | 0.07 g |
| Isotonic sodium chloride solution qs | 10.00 g |

The tinted ampoules are filled under an inert gas.

1 to 3 ampoules per day are administered to an adult individual for the treatment of severe cases of acne or psoriatic rheumatism, and a significant improvement is noted after approximately 30 days.

EXAMPLE 17

An aqueous alcoholic gel is prepared by producing the following formulation:

| | |
|---|---|
| Compound of Example 4 or 13 | 0.10 g |
| Ethanol | 50.00 g |
| Water | 48.00 g |
| Hydroxypropylcellulose | 2.00 g |

This gel is applied on skin of the type affected by acne, at the rate of 1 to 3 times daily, and a significant improvement is noted in a period of between 6 and 12 weeks, depending on the severity of the case treated.

EXAMPLE 18

A lotion is prepared by producing the following formulation:

| | |
|---|---|
| Compound of Example 6 or 4 | 0.01 g |
| Polyethylene glycol of molecular weight 400 | 59.99 g |
| Ethanol | 40.00 g |

This anti-seborrhoeic lotion is applied twice daily over an entire head of hair. A significant improvement is observed after 3 weeks of treatment.

This lotion can also be applied on greasy skin.

EXAMPLE 19

A water-removable ointment is prepared by producing the following formulation:

| | |
|---|---|
| Compound of Example 2 | 0.50 g |
| Polyethylene glycol of molecular weight 400 | 59.50 g |
| Polyethylene glycol of molecular weight 4000 | 25.00 g |
| Liquid paraffin | 15.00 g |

This ointment is applied twice daily on skin affected by ichthyosis, and a significant improvement is noted in a period of between 3 and 4 weeks, depending on the severity of the case treated.

EXAMPLE 20

A hydrophobic ointment having the following formulation is prepared:

| | |
|---|---|
| Compound of Example 8 | 1.00 g |
| Micronized silica | 10.00 g |
| Liquid paraffin | 89.00 g |

This ointment is applied twice daily on skin of the physiologically dry type, and a significant improvement is noted in a period of 15 days.

EXAMPLE 21

An anti-seborrhoeic lotion is prepared by producing the following formulation:

| | |
|---|---|
| Compound of Example 4 | 0.025 g |
| Propylene glycol | 5.000 g |
| Butylated hydroxytoluene | 0.100 g |
| Ethanol (95° strength) qs | 100.000 g |

This lotion is applied twice daily, and a significant improvement is noted in a period of between 2 and 6 weeks.

EXAMPLE 22

An anti-seborrhoeic cream is prepared by producing the following formulation:

| | |
|---|---|
| Polyoxyethylene stearate (40 moles of ethylene oxide) sold under the name "Myrj 52" by "Atlas" | 4 g |
| Mixture of lauric esters of sorbitol and sorbitan, polyoxyethyleneated with 20 moles of ethylene oxide, sold under the name "Tween 20" by "Atlas" | 1.8 g |
| Mixture of glycerol mono- and distearate sold under the name "GELEOL" by "GATTEFOSSE" | 4.2 g |
| Propylene glycol | 10 g |
| Butylated hydroxyanisole | 0.01 g |
| Butylated hydroxytoluene | 0.02 g |
| Cetyl/stearyl alcohol | 6.2 g |
| Preservatives qs | |
| Perhydrosqualene | 18 g |
| Mixture of caprylic/capric triglycerides sold under the name "Miglyol 812" by "Dynamit Nobel" | 4 g |
| S—carboxymethylcysteine | 3 g |
| Triethanolamine, 99% | 2.5 g |
| Compound of Example 10 | 0.02 g |
| Water qs | 100 g |

EXAMPLE 23

An anti-seborrhoeic cream is prepared by producing the following formulation:

| | |
|---|---|
| Polyoxyethylene stearate (40 moles of ethylene oxide) sold under the name "Myrj 52" by "Atlas" | 4 g |
| Mixture of lauric esters of Sorbitol and sorbitan, polyoxyethyleneated with 20 moles of ethylene oxide, sold under the name "Tween 20" by "Atlas" | 1.8 g |
| Mixture of glycerol mono- and distearate sold under the name "GELEOL" by "GATTEFOSSE" | 4.2 g |
| Propylene glycol | 10 g |
| Butylated hydroxyanisole | 0.01 g |
| Butylated hydroxytoluene | 0.02 g |
| Cetyl/stearyl alcohol | 6.2 g |
| Preservatives qs | |
| Perhydrosqualene | 18 g |
| Mixture of caprylic/capric triglycerides sold under the name "Miglyol 812" by "Dynamit Nobel" | 4 g |
| 2-(Benzylthio)ethylammonium 5-amino-5-carboxy-3-thiapentoate | 3 g |
| Compound of Example 13 | 0.05 g |
| Water qs | 100 g |

EXAMPLE 24

An anhydrous lotion is prepared by mixing the following ingredients:

| Ethanol | 45 g |
|---|---|
| Propylene glycol | 44.85 g |
| Polytetrahydrofuran dimethyl ether | 10 g |
| Compound of Example 9 | 0.1 g |
| Butylated hydroxytoluene | 0.05 g |

EXAMPLE 25

A filtering gel is prepared by mixing the following ingredients:

| Ethyl alcohol | 44 g |
|---|---|
| Propylene glycol | 44.07 g |
| Acrylic acid polymer sold under the name "CARBOPOL 940" by "GOODRICH CHEMICAL CO" | 1 g |
| Triethanolamine, 99% | 0.5 g |
| Butylated hydroxyanisole | 0.01 g |
| Butylated hydroxytoluene | 0.02 g |
| Purified water | 10 g |
| Compound of Example 13 | 0.10 g |
| 3,3'-Terephthalylidene-10,10'-dicamphosulphonic acid dihydrate | 0.5 g |

EXAMPLE 26

An anti-acne cream is prepared by mixing the following ingredients:

| Mixture of stearates of glycerol and polyethylene glycol (75 moles), sold under the name "GELOT 64" by "GATTEFOSSE" | 15 g |
|---|---|
| Kernel oil polyoxyethyleneated with 6 moles of ethylene oxide, sold under the name "Labrafil M 2130 CS" by "GATTFOSSE" | 8 g |
| Perhydrosqualene | 10 g |
| Colouring qs | |
| Preservatives qs | |
| Perfumes qs | |
| Tioxolone | 0.4 g |
| Polyethylene glycol of molecular mass 400 | 8 g |
| Purified water | 58.5 g |
| Ethylene diaminetetraacetic acid disodium salt | 0.05 g |
| Compound of Example 13 | 0.05 g |

EXAMPLE 27

A lotion for promoting the regrowth of hair is prepared by mixing the following ingredients:

| Propylene glycol | 20 g |
|---|---|
| Ethanol | 34.92 g |
| Polyethylene glycol of molecular mass 400 | 40 g |
| Water | 4 g |
| Butylated hydroxyanisole | 0.01 g |
| Butylated hydroxytoluene | 0.02 g |
| Compound of Example 10 | 0.05 g |
| Minoxidil | 1 g |

EXAMPLE 28

An anti-acne cream is prepared by mixing the following ingredients:

| Polyoxyethylene stearate (40 moles of ethylene oxide) sold under the name "Myrj 52" by "Atlas" | 4 g |
|---|---|
| Mixture of lauric esters of sorbitol and sorbitan, polyoxyethyleneated with 20 moles of ethylene oxide, sold under the name "Tween 20" by "Atlas" | 1.8 g |
| Mixture of glycerol mono- and distearate | 4.2 g |
| Propylene glycol | 10 g |
| Butylated hydroxyanisole | 0.01 g |
| Butylated hydroxytoluene | 0.02 g |
| Cetyl/stearyl alcohol | 6.2 g |
| Preservatives qs | |
| Polytetrahydrofuran dimethyl ether | 18 g |
| Mixture of caprylic/capric triglycerides sold under the name "Miglyol 812" by "Dynamit Nobel" | 4 g |
| Compound of Example 10 | 0.02 g |
| Water qs | 100 g |

EXAMPLE 29

An anti-acne gel is prepared by producing the following formulation:

| Compound of Example 10 | 0.10 g |
|---|---|
| Isopropyl alcohol | 40 g |
| Acrylic acid polymer sold under the name "CARBOPOL 940" by "GOODRICH CHEMICAL CO" | 1 g |
| Triethanolamine, 99% | 0.6 g |
| Butylated hydroxyanisole | 0.01 g |
| Butylated hydroxytoluene | 0.02 g |
| Tioxolone | 0.5 g |
| Propylene glycol | 8 g |
| Purified water qs | 100 g |

EXAMPLE 30

A filtering cream is prepared by producing the following formulation:

| Polyoxyethylene stearate (40 moles of ethylene oxide) sold under the name "Myrj 52" by "Atlas" | 4.4 g |
|---|---|
| Cetyl/stearyl alcohol | 6.2 g |
| Mixture of glycerol mono- and distearate sold under the name "GELEOL" by "GATTEFOSSE" | 4.3 g |
| Butylated hydroxyanisole | 0.05 g |
| Butylated hydroxytoluene | 0.05 g |
| Xanthan gum | 0.25 g |
| Isopropyl myristate | 4 g |
| Compound of Example 2 | 0.1 g |
| 3,3'-terephthalylidene-10,10'-dicamphosulphonic acid dihydrate | 2 g |
| Triethanolamine, 99% | 1 g |
| Demineralized water qs | 100 g |

EXAMPLE 31

A lotion for promoting the regrowth of hair is prepared by mixing the following ingredients:

| Propylene glycol | 13.96 g |
|---|---|
| Polyethylene glycol of molecular mass 300 | 40 g |
| Polyethylene glycol of molecular mass 1500 | 32 g |
| Isopropanol | 12 g |
| Butylated hydroxyanisole | 0.01 g |
| Butylated hydroxytoluene | 0.02 g |

|   |   |
|---|---|
| Compound of Example 4 | 0.01 g |
| Minoxidil | 2 g |

EXAMPLE 32

This is an anti-acne kit comprising two parts: (a) a gel is prepared by producing the following formulation:

|   |   |
|---|---|
| Ethyl alcohol | 48.4 g |
| Propylene glycol | 50 g |
| Acrylic acid polymer sold under the name "CARBOPOL 940" by "GOODRICH CHEMICAL CO" | 1 g |
| Diisopropanolamine, 99% | 0.3 g |
| Butylated hydroxyanisole | 0.05 g |
| Butylated hydroxytoluene | 0.05 g |
| α-Tocopherol | 0.1 g |
| Compound of Example 10 | 0.1 g |

In this part, the compound of Example 10 can be replaced by that of Example 2.

(b) a gel is prepared by producing the following formulation:

|   |   |
|---|---|
| Ethyl alcohol | 5 g |
| Propylene glycol | 5 g |
| Ethylenediaminetetraacetic acid disodium salt | 0.05 g |
| Acrylic acid polymer sold under the name "CARBAPOL 940" by "GOODRICH CHEMICAL CO" | 1 g |
| Triethanolamine, 99% | 1 g |
| Sodium lauryl sulphate | 0.1 g |
| Purified water | 75.05 g |
| Hydrated benzoyl peroxide, 25% strength | 12.8 g |

The mixing of the two gels will be carried out as required, weight for weight.

It is clearly understood that the examples described above are in no way limiting, and may give rise to any desirable modifications without thereby departing from the scope of the invention.

We claim:

1. A chemical compound having the formula

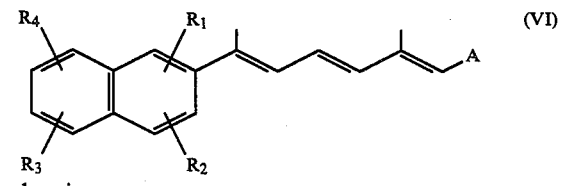

(VI)

wherein $R_1$, $R_2$, $R_3$, and $R_4$ are distributed on either of the rings or on both at once and are each, independently, selected from the group consisting of hydrogen, a linear or branched $C_1$-$C_6$ alkyl, OH and $C_1$-$C_6$ alkoxy; and A is selected from the group consisting of (i) —$COR_5$ wherein $R_5$ is selected from the group consisting of hydrogen when at least one of $R_1$ to $R_4$ is other than hydrogen; $C_1$-$C_6$ alkyl; amino; amino mono-or-disubstituted by $C_1$-$C_6$ alkyl or by $C_1$-$C_6$ alkyl mono-or polysubstituted by OH or by $C_1$-$C_6$ alkyl interrupted by one or more hetero atoms selected from the group consisting of O, S, and N, unsubstituted or substituted by one or more OH groups; arylamino; benzylamino; alicyclic amino; and N-heterocyclic amino radical, (ii) an amide group of an amino acid or of a glucosamine; and (iii) —$COOR_6$ wherein $R_6$ is selected from the group consisting of hydrogen, $C_1$-$C_6$ alkyl when one of $R_1$ to $R_4$ is other than hydrogen, $C_1$-$C_6$ mono- or polyhydroxyalkyl, aryl and benzyl, or $OR_6$ is (i') $C_6H_9O_6$ —radical derived from glucose, (ii') $C_6H_{11}O_6$ —radical derived from mannitol or (iii') $C_{11}H_9O_4$ —radical derived from erythritol;

or an isomer or salt thereof.

2. The compound of claim 1 wherein $R_1$, $R_2$, $R_3$, and $R_4$ are each independently selected from the group consisting of $C_1$-$C_6$ alkyl and $C_1$-$C_6$ alkoxy; and A is selected from the group consisting of amino and amino mono- or disubstituted by $C_1$-$C_6$ alkyl.

3. Compound according to claim 1, characterized in that the alkyl radicals which participate therein for the meanings of the radicals $R_1$ to $R_4$ are chosen from the group consisting of methyl, ethyl, isopropyl, butyl, isobutyl and hexyl radicals.

4. Compound according to one of claims 1 and 3, the said compound being a salt of a compound corresponding to the formula (VI) or of one of its isomers, characterized in that the said salt is a zinc salt, alkali metal or alkaline earth metal salt or salt of an organic amine, the compound of formula (VI) containing at least one free acid group.

5. A medicinal composition comprising in a pharmaceutically acceptable carrier at least one compound having the formula

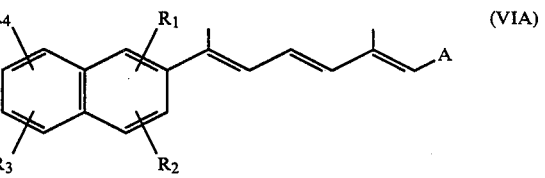

(VIA)

wherein $R_1$, $R_2$, $R_3$, and $R_4$ are distributed on either of the rings or on both at once and are each, independently, selected from the group consisting of hydrogen, a linear or branched $C_1$-$C_6$ alkyl, OH and $C_1$-$C_6$ alkoxy; and A is selected from the group consisting of (i) —$COR_5$ wherein $R_5$ is selected from the group consisting of hydrogen when at least one of $R_1$ to $R_4$ is other than hydrogen; $C_1$-$C_6$ alkyl; amino; amino mono- or disubstituted by $C_1$-$C_6$ alkyl or by $C_1$-$C_6$ alkyl mono-or polysubstituted by OH or by $C_1$-$C_6$ alkyl interrupted by one or more hetero atoms selected from the group consisting of O, S, and N, unsubstituted or substituted by one or more OH groups; arylamino; benzylamino; alicyclic amino; and N-heterocyclic amino radical, (ii) an amide group of an amino acid or of a glucosamine; and (iii) —$COOR_6$ wherein $R_6$ is selected from the group consisting of hydrogen, $C_1$-$C_6$ alkyl when one of $R_1$ to $R_4$ is other than hydrogen, $C_1$-$C_6$ mono- or polyhydroxyalkyl, aryl and benzyl, or $OR_6$ is (i') $C_6H_9O_6$ —radical derived from glucose, (ii') $C_6H_{11}O_6$ —radical derived from mannitol or (iii') $C_{11}H_9O_4$ —radical derived from erythritol;

or an isomer or salt thereof.

6. The composition of claim 5 for the treatment of dermatological conditions linked to a disorder of keratinization and dermatological or other conditions having an inflammatory or immuno-allergic component, or both, severe or extensive dermatological proliferations, for the treatment of rheumatic conditions, for the treatment of cutaneous atopy and respiratory atophy, for the treatment of epidermolysis bullosa dystrophica of the molecular pathology of collagen and solar carcinogenesis, of epidermal dysplasis verruciformis and for the treatment of an ophtalmological nature.

7. Composition according to claim 5, which can be used topically or for application to the eye, characterized in that the concentration of active substance(s) is between 0.0005% and 2% by weight.

8. Composition according to claim 5, characterized in that it can be administered topically, in the form of an ointment, gel, cream, pomade, powder, tincture, solution, suspension, emulsion, lotion, spray, patch and impregnated pad.

9. Composition according to claim 5, which can be used orally, characterized in that it is administered in the proportion of approximately 2 $\mu$g to 2 mg of active substance(s) per day per kg of body weight.

10. Composition according to claim 5, characterized in that it takes the form of a solution or suspension intended to be administered parenterally, in the proportion of 2 $\mu$g to 2 mg of active substance(s) per day per kg of body weight.

11. Composition according to claim 10, characterized in that it contains from 0.01 to 1 mg of active substance(s) per ml of solution or suspension.

12. Composition according to claim 5, characterized in that the pharmacologically acceptable carrier for the composition contains at least one product chosen from the group consisting of water, gelatin, lactose, starch, talc, vaseline, gum arabic, polyalkylene glycols, magnesium stearate, binders, fillers, diluents, solvents and thickeners.

13. A cosmetic composition comprising in a cosmetically acceptable carrier at least one compound of claim 1.

14. Composition according to claim 13 characterized in that it finds application in body and hair hygiene and in the treatment of skin which tends to be affected by acne, dry skin, seborrhoea and hair loss, to promote the regrowth of hair and for treatment and prevention against the deleterious effects of sunlight.

15. Composition according to claim 13 or 14, characterized in that the active substance(s) is/are present at a concentration of between 0.0005 and 2% by weight, and preferably between 0.01 and 1% by weight.

16. Composition according to claim 13, characterized in that it takes the form of a lotion, gel, cream, soap or shampoo.

17. Composition according to claims 5 or 13, characterized in that it contains inert or even pharmacodynamically or cosmetically active additives chosen from the group composed of moisturizing agents, anti-seborrhoeic and anti-acne agents, antibiotics, agents promoting regrowth of hair, anti-inflammatory agents, carotenoids, anti-psoriatic agents, flavouring agents, preservatives, stabilizers, moisture-regulating agents, pH-regulating agents, osmotic pressure-modifying agents, emulsifiers, UV-A and UV-B filters.

18. A process for preparing a compound having the formula

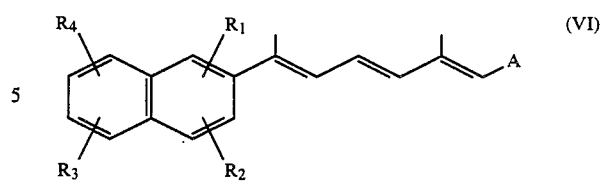

wherein
$R_1$, $R_2$, $R_3$, and $R_4$ are distributed on either of the rings or on both at once and are each, independently, selected from the group consisting of hydrogen, a linear or branched $C_1$-$C_6$ alkyl, OH and $C_1$-$C_6$ alkoxy; and A is selected from the group consisting of
(i) —$COR_5$ wherein $R_5$ is selected from the group consisting of hydrogen when at least one of $R_1$ to $R_4$ is other than hydrogen; $C_1$-$C_6$ alkyl; amino; mono- or disubstituted by $C_1$-$C_6$ alkyl or by $C_1$-$C_6$ alkyl mono- or polysubstituted by OH or by $C_1$-$C_6$ alkyl interrupted by one or more hetero atoms selected from the group consisting of O, S, and N, unsubstituted or substituted by one or more OH groups; arylamino; benzylamino; alicyclic amino; and N-heterocyclic amino radical, (ii) an amide group of an amino acid or of a glucosamine; and (iii) —$COOR_6$ wherein $R_6$ is selected from the group consisting of hydrogen, $C_1$-$C_6$ alkyl when one of $R_1$ to $R_4$ is other than hydrogen, $C_1$-$C_6$ mono- or polyhydroxyalkyl, aryl and benzyl, or $OR_6$ is (i') $C_6H_9O_6$ —radical derived from glucose, (ii') $C_6H_{11}O_6$ —radical derived from mannitol or (iii') $C_{11}H_9O_4$ —radical derived from erythritol;

or an isomer or salt thereof, said process comprising reacting in a basic medium a substituted or unsubstituted 2-[1-(triphenylphosphonio)ethyl]naphthalene salt having the formula

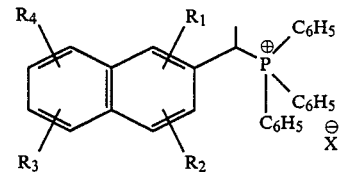

wherein
$R_1$, $R_2$, $R_3$, and $R_4$ are distributed on either of the rings or on both at once and are each, independently selected from the group consisting of hydrogen, a linear or branched $C_1$-$C_6$ alkyl, OH and $C_1$-$C_6$ alkoxy and X represents halogen, with an aldehyde RCHO wherein R represents
wherein A is

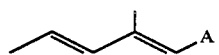

selected from the group consisting of
(i') —$COR_5$ wherein $R_5$ is selected from the group consisting of hydrogen when at least one of $R_1$ to $R_4$ is other than hydrogen; $C_1$-$C_6$ alkyl; amino mono- or disubstituted by $C_1$-$C_6$ alkyl; $C_1$-$C_6$ alkyl mono- or polysubstituted by OH; $C_1$-$C_6$ alkyl interrupted by one or more heteroatoms selected from the group consisting of O, S and N, unsubstituted or substituted by one or more OH groups; arylamino; benzylamino; alicyclic amino; and N-heterocyclic amino radical;

(ii') an amide group or an amino acid or of a glusosamine; and (iii') $-COOR_6$ wherein $R_6$ is selected from the group consisting of hydrogen, $C_1$–$C_6$ alkyl when on of $R_1$ to $R_4$ is other than hydrogen, $C_1$–$C_6$ mono- or polyhydroxyalkyl, aryl and benzyl, or $OR_6$ is (i") $C_6H_9O_6$ —radical derived from glucose, (ii") $C_6H_{11}O_6$ —radical derived from mannitol or (iii") $C_{11}H_9O_4$ —radical derived from erythritol.

* * * * *